United States Patent

Chan et al.

[11] Patent Number: 5,174,308
[45] Date of Patent: Dec. 29, 1992

[54] SMOKING COMPOSITIONS CONTAINING A PYRAZINEETHANOL FLAVORANT-RELEASE ADDITIVE

[75] Inventors: W. Geoffrey Chan, Chesterfield; Yoram Houminer, Richmond, both of Va.

[73] Assignees: Philip Morris Incorporated, New York, N.Y.; Philip Morris Products Inc., Richmond, Va.

[21] Appl. No.: 713,306

[22] Filed: Jun. 11, 1991

[51] Int. Cl.$^5$ .............................................. A24B 15/38
[52] U.S. Cl. ..................... 131/278; 131/274; 131/276
[58] Field of Search ......................... 131/274, 276, 278

[56] References Cited

U.S. PATENT DOCUMENTS

| | | | |
|---|---|---|---|
| 4,259,969 | 4/1981 | Houminer et al. | 131/278 |
| 4,312,367 | 1/1982 | Seeman | 131/276 |
| 4,312,368 | 1/1982 | Houminer et al. | 131/278 |

Primary Examiner—Paul Prebilic
Attorney, Agent, or Firm—James E. Schardt

[57] ABSTRACT

This invention provides smoking compositions which contain a novel flavorant-release additive.

Under cigarette smoking conditions, a combustible filler and/or paper wrapper additive such as 2-(3-hexyl-2-hydroxy-4-phenyl-3-buten-1-yl)--3,5,6-trimethylpyrazine releases pyrazine and cinnamaldehyde type of volatile flavorants into the cigarette smoke:

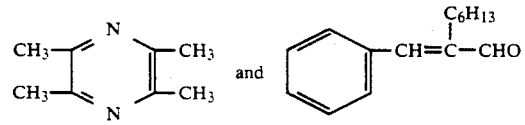

A present invention flavorant-release additive is represented by the formula

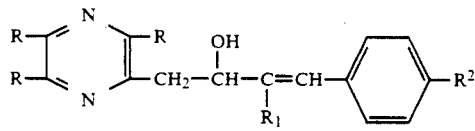

where R is hydrogen or methyl, $R^1$ is hydrogen or a $C_1$-$C_{10}$ alkyl substituent; and $R^2$ is hydrogen or a $C_1$-$C_4$ alkyl or $C_1$-$C_4$ alkoxy substituent.

22 Claims, No Drawings

SMOKING COMPOSITIONS CONTAINING A PYRAZINEETHANOL FLAVORANT-RELEASE ADDITIVE

BACKGROUND OF THE INVENTION

It has been established that alkylpyrazines are natural components of tobacco smoke, and that they are contributors to tobacco smoke flavor [A. Baggett et al J. Chromatog. 97, 79 (1974)]. 2-Isopropenylpyrazine has been identified as a tobacco flavorant constituent of burley tobacco [E. Demole et al, Helv. Chem. Acta, 55, 1866 (1972)].

Patents which disclose the addition of various pyrazine compounds to tobacco and foodstuffs as a means of providing flavor or flavor enhancement include U.S. Pat. Nos. 3,684,809; 3,705,158; 3,754,934; 3,764,349; 3,767,426; and 3,881,025.

It is characteristic of pyrazine and pyridine and other heteroaromatic derivatives employed as tobacco flavorants in the prior art that the respective derivatives have the disadvantage of both high volatility and low odor threshold. Both of these properties significantly restrict the extent that these heteroaromatic derivatives can be utilized as flavorants in tobacco compositions. A quantity of a pyrazine or pyridine derivative in a tobacco composition sufficient to have a noticeable effect in low delivery cigarettes causes a marked pack aroma.

U.S. Pat. No. 4,259,969 endeavors to overcome some of the disadvantages of the above-described flavorant technology. The patent describes smoking composition flavorant-release additives which are not volatile at ambient temperatures, such as 2-(2-hydroxy-2-phenylethyl)-3,5,6-trimethylpyrazine and related derivatives corresponding to the formula:

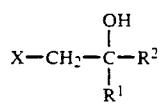

wherein X is selected from pyrazine and pyridine radicals corresponding to the chemical structures:

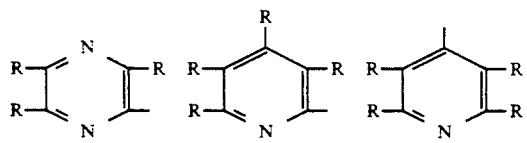

where R is hydrogen or methyl; $R^1$ is hydrogen or $C_1$-$C_{10}$ alkyl; $R^2$ is a substituent selected from aliphatic, alicyclic and aromatic groups containing about 1–12 carbon atoms; and $R^1$ and $R^2$ when taken together with connecting elements form an alicyclic structure.

Other smoking composition developments of interest with respect to the present invention are those in which an organic additive is utilized that releases at least two flavorants which are organoleptically compatible, and enhance the flavor and aroma of cigarette smoke.

U.S. Pat. Nos. 4,036,237; 4,141,906; and 4,178,458 describe β-hydroxyesters which as additives in smoking compositions pyrolyze into volatile aldehyde and ester flavorants under smoking conditions.

U.S. Pat. Nos. 4,473,085 and 4,607,118 describe β-hydroxyesters which as additives in smoking compositions pyrolyze into volatile ketone and ester flavorants under smoking conditions.

U.S. Pat. No. 4,312,368 describes smoking compositions which contain a heterocyclic-hydroxy-substituted carboxylate flavorant-release additive such as ethyl 2-(2-butyl)-3-hydroxy-3-methyl-3-(3-pyridyl)propionate. Under smoking conditions this additive pyrolyzes into 3-acetylpyridine and ethyl β-methylvalerate flavorants.

There is continuing research effort to develop improved smoking compositions which generate smoke with flavorant-enhanced taste and character under smoking conditions.

Accordingly, it is an object of this invention to provide smoking compositions having incorporated therein a flavorant component which is characterized by lack of mobility and/or volatility at ambient temperature.

It is another object of this invention to provide smoking compositions having incorporated therein a flavorant-release additive which under normal smoking conditions imparts improved flavor to mainstream smoke and improved aroma to sidestream smoke.

It is a further object of this invention to provide novel organic compounds which are adapted to be incorporated into cigarette fillers and/or paper wrappers, and which under normal smoking conditions release volatile pyrazine and cinnamaldehyde type flavorant constituents into cigarette smoke.

Other objects and advantages of the present invention shall become apparent from the following description and examples.

DESCRIPTION OF THE INVENTION

One or more objects of the present invention are composition comprising an admixture of (1) combustible filler selected from natural tobacco, reconstituted tobacco and tobacco substitutes, and (2) between about 0.0001–5 weight percent, based on the total weight of filler, of a flavorant-release additive corresponding to the formula:

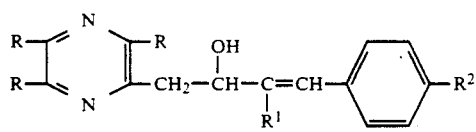

where R is hydrogen or methyl, $R^1$ is hydrogen or a $C_1$-$C_{10}$ alkyl substituent; and $R^2$ is hydrogen or a $C_1$-$C_4$ alkyl or $C_1$-$C_4$ alkoxy substituent.

In another embodiment this invention provides a cigarette smoking product comprising (1) a combustible filler selected from natural tobacco, reconstituted tobacco and tobacco substitutes, and (2) a paper wrapper which has incorporated therein a flavorant-release additive corresponding to the formula:

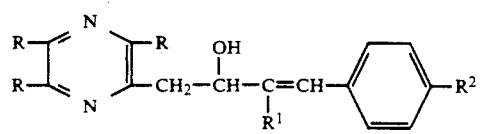

where R is hydrogen or methyl, $R^1$ is hydrogen or a $C_1$-$C_{10}$ alkyl substituent; and $R^2$ is hydrogen or a $C_1$-$C_4$ alkyl or $C_1$-$C_4$ alkoxy substituent.

Illustrative of $C_1$–$C_4$ alkyl and alkoxy substituents in the above represented flavorant-release additive formula I are methyl, ethyl, propyl, 2propyl, butyl, 2-butyl and isobutyl groups, and the corresponding alkoxy structures.

Illustrative of $C_1$–$C_{10}$ alkyl substituents in formula I are the above recited $C_1$–$C_4$ alkyl groups, and additionally structures such as pentyl, 2-pentyl, hexyl, 2-hexyl, heptyl, octyl, isooctyl, nonyl and decyl groups.

A cigarette smoking product in accordance with the present invention typically contains between about 0.01–5 weight percent of flavorant-release additive in the paper wrapper, based on the weight of combustible filler.

In a further embodiment an invention cigarette product contains between about 0.01–5 weight percent of flavorant-release additive in the paper wrapper, and contains between about 0.0001–5 weight percent of flavorant-release additive in the combustible filler.

A present invention flavorant-release additive in accordance with formula I which is incorporated in smoking compositions as described above is a low volatility compound which under normal smoking conditions pyrolyzes into volatile constituents which enhance the flavor and aroma of low delivery cigarette smoke:

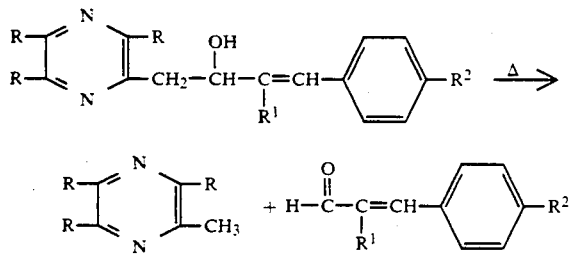

where R, $R^1$ and $R^2$ are as previously defined.

An important feature of an invention smoking composition having a formula I additive is the release of two flavorants under smoking conditions, one of which is a pyrazine and the other is a cinnamaldehyde type compound.

Both the pyrazine and cinnamaldehyde volatiles which are released have desirable organoleptic properties. Each of the compounds contributes a pleasant flavor and aroma to cigarette smoke. The pyrolysis of a present invention flavorant compound proceeds smoothly and quantitatively at a temperature as low as 175° C.

In another embodiment this invention provides a novel class of pyrazineethanol compounds corresponding to the formula:

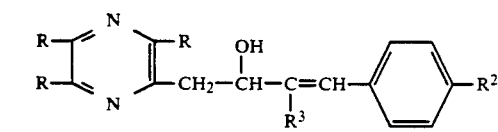

where R is hydrogen or methyl, $R^2$ is hydrogen or a $C_1$–$C_4$ alkyl or $C_1$–$C_4$ alkoxy substituent; and $R^3$ is a $C_5$–$C_{10}$ alkyl substituent.

The formula II pyrazineethanol compounds exhibit unique properties when utilized as a flavorant-release additive in a present invention smoking composition. In addition to imparting a pleasing flavor and aroma to cigarette smoke, a formula II flavorant-release additive tends to mellow the harsh tone which is characteristic of sidestream smoke.

An important advantage of a present invention flavorant-release compound is an excellent stability property when utilized as a cigarette paper additive and the paper is exposed to variable conditions of light and moisture. Cigarette paper treated with a present invention flavorant-release additive does not discolor under light and moisture exposure conditions due to decomposition of the additive.

PREPARATION OF FLAVORANT-RELEASE COMPOUNDS

A preferred method of preparing a formula I type of pyrazineethanol structure is by the reaction of a methylpyrazine derivative with an aldehyde derivative, both of which are appropriately substituted:

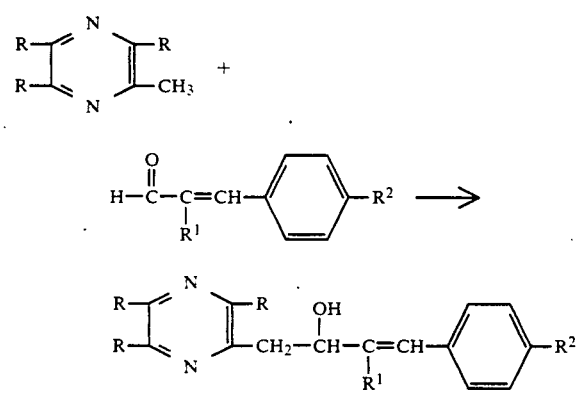

The reaction is conducted in the presence of a strong base such as phenyllithium, lithium diisopropylamide or alkali metal hydride. The strong base initiates the in situ formation of a pyrazylmethylene anion.

Preferably, the base is added to the pyrazine starting material in an inert solvent medium maintained at a temperature between about 0° C. and 50° C. and under an inert atmosphere. This procedure is followed by the addition of the aldehyde compound to the reaction medium at a temperature between about −65° C. and 25° C. The resultant hydroxyethyl-substituted pyrazine product typically is an odorless, white crystalline solid.

PREPARATION OF SMOKING COMPOSITIONS

In a further embodiment, this invention provides a method of preparing a smoking composition which is adapted to impart flavor and aroma to mainstream and sidestream smoke under smoking conditions, which method comprises incorporating into natural tobacco, reconstituted tobacco or tobacco substitute between about 0.0001–5 weight percent, based on composition weight, of a flavorant-release additive corresponding to formula I as previously defined above.

The invention flavorant-release additive can be incorporated into the tobacco or tobacco substitute in accordance with methods known and used in the art. Preferably the flavorant-release additive is dissolved in a solvent such as alcohol or aqueous alcohol and then sprayed or injected into the tobacco and/or tobacco substitute matrix. Such method ensures an even distribution of the flavorant additive throughout the filler, and thereby facilitates the production of a more uniform smoking composition. Alternatively, the additive may be incorporated as part of a concentrated tobacco extract which is applied to a fibrous tobacco web as in the manufacture of reconstituted tobacco. Another suitable procedure is to incorporate the additive in tobacco or tobacco substitute filler in a concentration between about 0.5–5 weight percent, based on the weight of filler, and then subsequently to blend the treated filler with filler which does not contain additive.

The term "tobacco substitute" is meant to include non-tobacco smoking filler materials such as are disclosed in U.S. Pat. Nos. 3,703,177; 3,796,222; 4,019,521; 4,079,742; and references cited therein; incorporated herein by reference.

As previously described hereinabove, an invention flavorant-release additive also can be incorporated in the paper wrapper of cigarette products, for the purpose of enhancing the aroma of cigarette sidestream smoke under smoking conditions. The incorporation can be accomplished by coating the paper wrapper with a solvent solution of the flavorant-release additive, utilizing a size press or other conventional coating equipment. The flavorant-release additive also can be incorporated as a constituent of the composition used as a paper wrapper sideseam adhesive.

The following Examples are further illustrative of the present invention. The specific ingredients and processing parameters are presented as being typical, and various modifications can be derived in view of the foregoing disclosure within the scope of the invention.

EXAMPLE I 2-(3-Hexyl-2-hydroxy-4-phenyl-3-buten-1-yl)-3,5,6-trimethylpyrazine

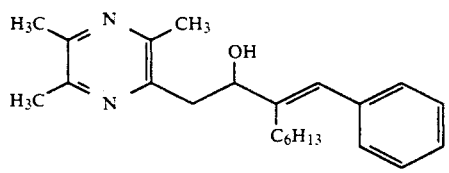

To a solution of lithium diisopropylamide (1.5 Molar, 73.3 mL, 0.11 mole) in 150 mL of tetrahydrofuran at −78° C. is added slowly a solution of tetramethylpyrazine (13.6 g, 0.1 mole) in 100 mL of tetrahydrofuran. The mixture is allowed to warm to room temperature and then cooled to −78° C. A solution of α-hexylcinnamaldehyde (23.7 g, 0.11 mole) in 100 mL of tetrahydrofuran is added dropwise over 15 minutes. The solution is allowed to warm to room temperature, and then poured into an ice/dilute hydrochloric acid mixture. The organic layer is separated and washed with saturated solutions of sodium bicarbonate and sodium chloride. The solution is dried over anhydrous magnesium sulfate. After filtration of drying agent and evaporation of solvent, a yield of 40 g of crude material is obtained. A volatile fraction in the crude material is removed by distillation at below 85° C. under 0.15 torr of mercury. The residue is crystallized from a mixture of ethyl acetate-hexane. The product is obtained as a fine needle, M.P. 61°–62° C. Yield 26 g (70%). NMR and IR confirm the structure.

Anal. Calc. for $C_{23}H_{32}N_2O$: C,78.37;H, 9.15;N, 7.95. Found: C,78.37;H,9.14;N,7.83.

EXAMPLE II 2-(2-Hydroxy-4-phenyl-3-buten-1-yl)-3 5.6-trimethylpyrazine

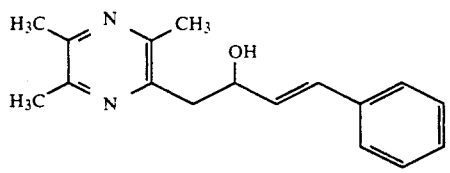

To a solution of lithium diisopropylamide (1.5 Molar, 73.3 mL, 0.11 mole) in 150 mL of tetrahydrofuran at −78° C. is added slowly a solution of tetramethylpyrazine (13.6 g, 0.1 mole) in 100 mL of tetrahydrofuran. The mixture is allowed to warm to room temperature and then cooled to −78° C. A solution of cinnamaldehyde (14.5 g, 0.11 mole) in 100 mL of tetrahydrofuran is added dropwise over 15 minutes. The reaction product mixture is then worked up according to the procedures of Example I to provide the title compound.

EXAMPLE III 2-(3-Hexyl-2-hydroxy-4-phenyl-3-buten-1-yl)-3-methylpyrazine

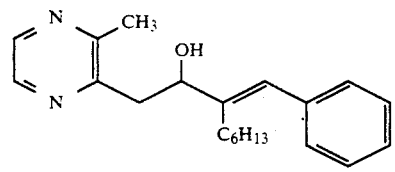

To a solution of lithium diisopropylamide (1.5 Molar, 73.3 mL, 0.11 mole) in 150 mL of tetrahydrofuran at −78° C. is added slowly to a solution of 2,3-dimethylpyrazine (10.8 g, 0.1 mole) in 100 mL of tetrahydrofuran. The mixture is allowed to warm to room temperature and then cooled to −78° C. A solution of α-hexylcinnamaldehyde (23.7 g, 0.11 mole) in 100 mL of tetrahydrofuran is added dropwise over 15 minutes. The reaction product mixture is then worked up according to the procedures of Example I to provide the title compound.

EXAMPLE IV 2-(2-Hydroxy-4-phenyl-3-buten-1-yl)-6-methylpyrazine

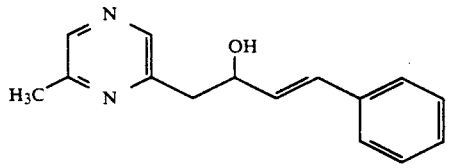

To a solution of lithium diisopropylamide (1.5 Molar, 73.3 mL, 0.11 mole) in 150 mL of tetrahydrofuran at −78° C. is added slowly a solution of 2,6-dimethylpyrazine (10.8 g, 0.1 mole) in 100 mL of tetrahydrofuran. The mixture is allowed to warm to room temperature and then cooled to −78° C. A solution of cinnamaldehyde (14.5 g, 0.11 mole) in 100 mL of tetrahydrofuran is added dropwise over 15 minutes. The reaction product mixture is then worked up according to the procedures of Example I to provide the title compound.

EXAMPLE V 2-(2-Hydroxy-4-p-methoxyphenyl-3-buten-1-yl)-3,5,6-trimethylpyrazine

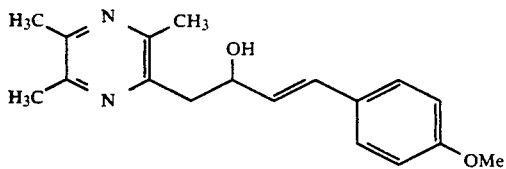

To a solution of lithium diisopropylamide (1.5 Molar, 73.3 mL, 0.11 mole) in 150 mL of tetrahydrofuran at −78° C. is added slowly a solution of tetramethylpyrazine (13.6 g, 0.1 mole) in 100 mL of tetrahydrofuran. The mixture is allowed to warm to room temperature and then cooled to −78° C. A solution of p-methoxycinnamaldehyde (17.8 g, 0.11 mole) in 100 mL of tetrahydrofuran is added dropwise over 15 minutes. The reaction product mixture is then worked up according to the procedures of Example I to provide the title compound.

EXAMPLE VI 2-(2-Hydroxy-4-p-methoxyphenyl-3-buten-1-yl)pyrazine

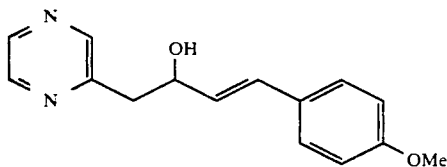

To a solution of lithium diisopropylamide (1.5 Molar, 73.3 mL, 0.11 mole) in 150 mL of tetrahydrofuran at −78° C. is added slowly to a solution of 2-methylpyrazine (9.4 g, 0.1 mole) in 100 mL of tetrahydrofuran. The mixture is allowed to warm to room temperature and then cooled to −78° C. A solution of p-methoxycinnamaldehyde (17.8 g, 0.11 mole) in 100 mL of tetrahydrofuran is added dropwise over 15 minutes. The reaction product mixture is then worked up according to the procedure of Example I to provide the title compound.

EXAMPLE VII

A 2% solution of the Example I compound in 95% ethanol is applied to the paper wrapper of cigarettes to obtain about 0.5 mg of the compound per cigarette. The cigarettes are smoked and evaluated by an experienced smoking panel in comparison to untreated control cigarettes. The treated cigarettes exhibit pleasant herbal-spicy aromas in the sidestream smoke without a significant change in the taste of the cigarettes (mainstream smoke).

What is claimed is:

1. A smoking composition comprising an admixture of (1) combustible filler selected from natural tobacco, reconstituted tobacco and tobacco substitutes, and (2) between about 0.0001–5 weight percent, based on the total weight of filler, of a flavorant-release additive corresponding to the formula:

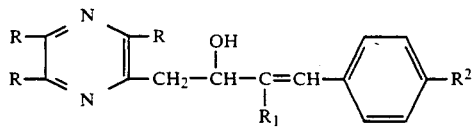

where R is hydrogen or methyl, $R^1$ is hydrogen or a $C_1$–$C_{10}$ alkyl substituent; and $R^2$ is hydrogen or a $C_1$–$C_4$ alkyl or $C_1$–$C_4$ alkoxy substituent.

2. A smoking composition in accordance with claim 1 wherein the flavorant-release additive is 2-(3-hexyl-2-hydroxy-4-phenyl-3-buten-1-yl)-3,5,6-trimethylpyrazine.

3. A smoking composition in accordance with claim 1 wherein the flavorant-release additive is 2-(2-hydroxy-4-phenyl-3-buten-1-yl)-3,5,6-trimethylpyrazine.

4. A smoking composition in accordance with claim 1 wherein the flavorant-release additive is 2-(3-hexyl-2-hydroxy-4-phenyl-3-buten-1-yl)-3--methylpyrazine.

5. A smoking composition in accordance with claim 1 wherein the flavorant-release additive is 2-(2-hydroxy-4-phenyl-3-buten-1-yl)-6-methylpyrazine.

6. A smoking composition in accordance with claim 1 wherein the flavorant-release additive is 2-(2-hydroxy-4-p-methoxyphenyl-3-buten-1-yl)-3,5,6-trimethylpyrazine.

7. A smoking composition in accordance with claim 1 wherein the flavorant-release additive is 2-(2-hydroxy-4-p-methoxyphenyl-3-buten-1-yl)-pyrazine.

8. A cigarette smoking product comprising (1) a combustible filler selected from natural tobacco, reconstituted tobacco and tobacco substitutes, and (2) a paper wrapper which has incorporated therein a flavorant-release additive corresponding to the formula:

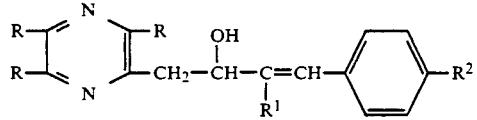

where R is hydrogen or methyl, $R^1$ is hydrogen or a $C_1$–$C_{10}$ alkyl substituent; and $R^2$ is hydrogen or a $C_1$–$C_4$ alkyl or $C_1$–$C_4$ alkoxy substituent.

9. A cigarette smoking product in accordance with claim 8 wherein the paper wrapper contains between about 0.01–5 weight percent of flavorant-release additive.

10. A cigarette smoking product in accordance with claim 8 wherein the flavorant-release additive in the paper wrapper is 2-(3-hexyl-2-hydroxy-4-phenyl-3-buten-1-yl)-3,5,6-trimethylpyrazine.

11. A cigarette smoking product in accordance with claim 8 wherein the flavorant-release additive in the paper wrapper is 2-(2-hydroxy-4-phenyl-3-buten-1-yl)-3,5,6-trimethylpyrazine.

12. A cigarette smoking product in accordance with claim 8 wherein the flavorant-release additive in the paper wrapper is 2-(3-hexyl-2-hydroxy-4-phenyl-3-buten-1-yl)-3-methylpyrazine.

13. A cigarette smoking product in accordance with claim 8 wherein the flavorant-release additive in the paper wrapper is 2-(2-hydroxy-4-phenyl-3-buten-1-yl)-6-methylpyrazine.

14. A cigarette smoking product in accordance with claim 8 wherein the flavorant-release additive in the paper wrapper is 2-(2-hydroxy-4-p-methoxyphenyl-3-buten-1-yl) -3,5,6-trimethylpyrazine.

15. A cigarette smoking composition in accordance with claim 8 wherein the flavorant-release additive in the paper wrapper is 2-(2-hydroxy-4-p-methoxyphenyl-3-buten-1-yl) -pyrazine.

16. A cigarette smoking product in accordance with claim 8 wherein the combustible filler contains between about 0.0001–15 weight percent, based on the weight of filler, of a flavorant-release additive corresponding to the formula:

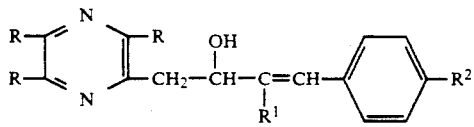

where R is hydrogen or methyl, $R^1$ is hydrogen or a $C_1$–$C_{10}$ alkyl substituent; and $R^2$ is hydrogen or a $C_1$–$C_4$ alkyl or $C_1$–$C_4$ alkoxy substituent.

17. A cigarette smoking product in accordance with claim 16 wherein the flavorant-release additive in the combustible filler is 2-(3-hexyl-2-hydroxy-4-phenyl-3-buten-1-yl)-3,5,6-trimethylpyrazine.

18. A cigarette smoking product in accordance with claim 16 wherein the flavorant-release additive in the combustible filler is 2-(2-hydroxy-4-phenyl-3-buten-1-yl) -3,5,6-trimethylpyrazine.

19. A cigarette smoking product in accordance with claim 16 wherein the flavorant-release additive in the combustible filler is 2-(3-hexyl-2-hydroxy-4-phenyl-3-buten -1-yl)-3-methylpyrazine.

20. A cigarette smoking product in accordance with claim 16 wherein the flavorant-release additive in the combustible filler is 2-(2-hydroxy-4-phenyl-3-buten-1-yl)-6-methylpyrazine.

21. A cigarette smoking product in accordance with claim 16 wherein the flavorant-release additive in the combustible filler is 2-(2-hydroxy-4-p-methoxyphenyl-3-buten-1-yl)-3,5,6-trimethylpyrazine.

22. A cigarette smoking product in accordance with claim 16 wherein the flavorant-release additive in the combustible filler is 2-(2-hydroxy-4-p-methoxyphenyl-3-buten-1-yl)-pyrazine.

* * * * *